(12) United States Patent
Fuhr et al.

(10) Patent No.: US 6,542,778 B1
(45) Date of Patent: Apr. 1, 2003

(54) PROCESS AND DEVICE FOR PERMEATION OF BIOLOGICAL OBJECTS

(75) Inventors: Günter Fuhr, Berlin (DE); Ulrich Zimmermann, Waldbrunn (DE); Rolf Hagedorn, Berlin (DE)

(73) Assignee: Evotec OAI AG. (DE)

( * ) Notice: Subject to any disclaimer, the term of this patent is extended or adjusted under 35 U.S.C. 154(b) by 0 days.

(21) Appl. No.: 09/718,797

(22) Filed: Nov. 22, 2000

Related U.S. Application Data

(63) Continuation of application No. PCT/EP99/03442, filed on May 19, 1999.

(30) Foreign Application Priority Data

May 22, 1998 (DE) .................................. 198 23 047

(51) Int. Cl.$^7$ ................................. A61N 1/18
(52) U.S. Cl. ........................... 607/72; 607/74
(58) Field of Search ............... 604/20, 44; 607/2, 607/3, 50, 66, 67, 70, 72, 73, 74

(56) References Cited

U.S. PATENT DOCUMENTS

| | | | | |
|---|---|---|---|---|
| 4,406,658 A | * | 9/1983 | Lattin et al. | 604/20 |
| 4,622,302 A | * | 11/1986 | Sowers | 435/172.2 |
| 4,764,473 A | | 8/1988 | Matschke et al. | |
| 4,822,470 A | * | 4/1989 | Change | 204/299 R |
| 5,224,927 A | * | 7/1993 | Tapper | 604/20 |
| 6,029,090 A | * | 2/2000 | Herbst | 607/66 |
| 6,264,815 B1 | * | 6/2001 | Pethig et al. | 204/547 |

FOREIGN PATENT DOCUMENTS

| | | |
|---|---|---|
| DE | 44 11 333 A1 | 8/1995 |
| EP | 0 126 389 | 11/1984 |
| EP | 0 710 718 A1 | 5/1996 |
| JP | 60-251874 | 12/1985 |
| JP | 60-251877 | 12/1985 |
| JP | 61-111680 | 5/1986 |
| JP | 63-049071 | 1/1988 |
| WO | WO 98/56893 | 12/1998 |

\* cited by examiner

*Primary Examiner*—Jeffrey R. Jastrzab
*Assistant Examiner*—Frances P. Oropeza
(74) *Attorney, Agent, or Firm*—Schnader Harrison Segal & Lewis LLP

(57) ABSTRACT

A process for treating a biological or synthetic object subjected to an electrical field in a surrounding liquid medium for a predetermined pulse time (t1), the electrical field being formed by at least two electrodes including actuating at least once during the pulse time (t1) each of the electrodes as an anode and as a cathode, to cause at each electrode a polarity reversal and alternating electrolytic increases and reductions in pH of at least a portion of the liquid medium, subjecting the object during the pulse time (t1) to a number of electrical partial pulses which have a frequency in the range of 1 kHz to 1 MHz and which possess partial pulse durations, with sequentially reversing polarity or field direction such that the partial pulses possess sequentially varying partial pulse durations (t11, t12), pulse forms, and/or pulse amplitudes, and selecting the partial pulse durations (t11, t12), pulse forms, and/or pulse amplitudes such that, due to the electrolytic increases and reductions in pH value, substantially equal H$^+$ and OH$^-$ ion concentrations are created.

12 Claims, 3 Drawing Sheets

PROCESS AND DEVICE FOR PERMEATION OF BIOLOGICAL OBJECTS

RELATED APPLICATION

This is a continuation of International Application No. PCT/EP99/03442, with an international filing date of May 19, 1999, which is based on German Patent Application No. 198 23 047.8, filed May 22, 1998.

FIELD OF THE INVENTION

This invention relates to a process for the manipulation or processing of biological objects by means of electrical pulses, in particular, for the permeation and/or fusion of cells or of synthetic, membrane-encased structures such as liposoma or vesicles, or for the permeation of membrane or layered materials in electrode structures, and devices for the implementation of the process.

BACKGROUND

With many biotechnological, medical, or genetic tasks, the short-term and reversible increase in the permeability of the covering of living cells suspended in a fluid is of interest (overview in "Electromanipulation of Cells", U. Zimmermann, G. A. Neil, CRC, 1996). In addition to chemical and virus-based methods, the simplicity and definability of the application have caused permeabilization by means of short electrical pulses to come to prominence. The process is designated as "electroporation," "electropermeation," or also "electropermeabilization," and is implemented with commercially available equipment from a number of manufacturers.

In conventional electroporation devices, the cells which are to be manipulated are suspended in a solution in a cuvette between electrodes for the application of electrical pulses. What all the devices have in common is the use of one or more electrical pulses of an amplitude of between 10 V up to several 1000 V. The pulse form depends on the device. The pulse duration is selected dependent on the object (dependent on the size in particular), and lies in the range from a few μs up to several 100 ms. The electrodes (in most cases two) are in each case permanently connected in pairs, as cathode and anode, respectively.

One serious problem of electropermeabilization which has not hitherto been solved lies in the fact that the pH in the vicinity of the electrodes changes locally due to electrolysis manifestations which are not temporally stationary, with the result that sustained interference in the poration conditions occurs. Depending on the composition of the solution, subjecting the electrodes to electrical pulses leads to creation of $H^+$ (protons) or $OH^-$ (hydroxyl ions) enrichment ("clouds") and, therefore, to a local acidic or alkaline area. As the pulse duration increases, a front of low or high pH value migrates from one electrode to the other. Even if the pH changes in the areas of the two electrodes are virtually neutralised over the entire fluid filling of the cuvette, the cells of the individual spatial areas are subjected to a pH gradient and change of up to 5 pH units, which can lead to a substantial influence on the life processes, up to the stage of devitalization and initiation of apoptosis.

In addition to this, the local pH changes may cause undesirable electrode reactions. If, for example, aluminium is used as the electrode material, there is the possibility of aluminium being resolved when the pulses are applied, and poisoning the cell suspension. This problem can indeed be solved by use of noble metals as the electrode materials. However, the result of this is that an electroporation device becomes very expensive.

With the known pulse techniques (capacitor discharge, square-wave pulse, delta pulse, etc.) it is not possible for the pH stress of the cells to be avoided, since this involves fundamental phenomenon at the anode and cathode. There have indeed been attempts before now to minimize the electrolysis effect by application of very short pulses. As a result, however, usability of the electroporation process is limited.

Particularly with objects with widely deposited layers, such as bacteria, longer pulse times are, however, more effective, so that pH changes have a particularly negative effect, and there is a need for alternative techniques without losing the advantage of the electrical field application.

A method for cell poration and fusion using electrical high frequency pulses is known from EP 0 710 718 A1. For pulse treatment, an electrode pair is subjected to high frequency voltages, whereby one electrode of the electrode pair has ground potential while the other electrode is subjected to a high frequency alternating voltage.

Thus, it would be advantageous to provide a process which is an improvement on conventional permeabilization systems, based on the electrical pulse technology. This would be characterised in particular by a reduced or almost compensated pH change stress on the cells, and the suppression of electrode reactions. It would be advantageous to provide a device for implementing the process, with which the possibilities of use of the electropermeation techniques referred to can be extended and the efficiency of the permeation or cell fusion can be increased.

SUMMARY OF THE INVENTION

The invention relates to a process for treating a biological or synthetic object subjected to an electrical field in a surrounding medium for a predetermined pulse time (t1), the electrical field being formed by at least two electrodes, whereby during the pulse time (t1) each of the electrodes is actuated at least once as the anode and at least once as the cathode, to cause at each electrode a polarity reversal and alternating electrolytic increases and reductions in pH of at least a portion of the object, wherein the object is subjected during the pulse time (t1) to a number of electrical partial pulses which possess partial pulse durations, with sequentially reversing polarity or field direction, whereby the partial pulses possess sequentially varying partial pulse durations (t11, t12), pulse forms, and/or pulse amplitudes, and the partial pulse durations (t11, t12), pulse forms, and/or pulse amplitudes are selected such that, due to the electrolytic increases and reductions in pH value, substantially equal $H^+$ and $OH^-$ ion concentrations are created.

The invention also relates to a device for treating a biological or synthetic object in a surrounding medium between at least two electrodes, which are connected to a pulse generator, wherein the pulse generator is connected to the electrodes via a control circuit arranged to impose on the electrodes, during a predetermined pulse time, at least two partial pulses of alternating reversed polarity or field direction, whereby the pulse generator provides the partial pulses in digitalized form for creation of asymmetries in pulse height, pulse path, or pulse length.

BRIEF DESCRIPTION OF THE DRAWINGS

Further advantages and details of the invention are explained hereinafter, by reference to the appended drawings. These show.

DETAILED DESCRIPTION OF THE INVENTION

Figure 1A:
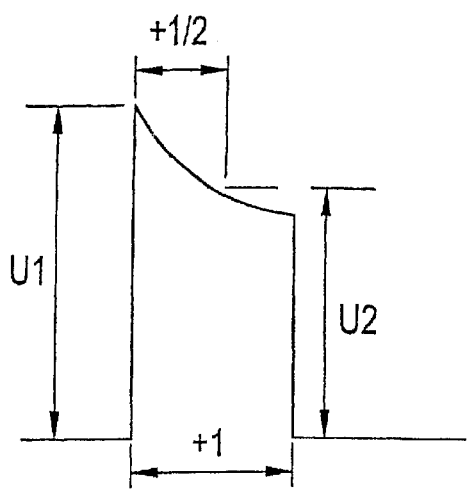
FIGS. 1A, 1B: a representation of splitting according to the invention of an exponential poration pulse into partial pulses.

The following description is intended to refer to specific embodiments of the invention illustrated in the drawings and is not intended to define or limit the invention, other than in the appended claims.

The invention is based on the idea of departing from the previous concept of wiring electrodes as anode and cathode, respectively, and, instead, to change at least once the polarity of the electrodes and the field direction, respectively, during the pulse period of each treatment or poration. As a result, sequentially changing and mutually compensating electrolytic rises and falls of the pH are achieved at each electrode. With the use, for example, of two electrodes, each electrode is operated during the set pulse period (which typically lies in the is to ms range) at least once as cathode and once as anode. In order to achieve this, the pulse is broken down into individual or partial pulses of opposed polarity which follow one another very rapidly, or an electronic gate circuit is introduced, which allows for an electrical change-over signal to be coupled as a pulse package, or for the wiring of the pulse electrodes in the $\mu$s range to be changed.

The term cathode or anode in this case designates the electrode with the more positive or more negative potential. The invention can be put into effect with potential-differentiated pulses irrespective of their absolute potential position.

The change-over pulse technique according to the invention is based in particular on the following considerations. With application of an electrical field or poration pulse of a predetermined pulse period (e.g. about 50 $\mu$s) for cell permeation between two electrodes, with the decomposition of the poration pulse into two partial pulses of differing polarity (in each case with the half pulse duration (e.g. about 25 $\mu$s) or with another part relationship), which follow one another essentially immediately, each of the electrodes takes effect once as anode and as cathode. This creates proton and hydroxyl ion clouds which follow one another more rapidly than they can disperse from the electrodes, so that they are already neutralized and attenuated within a range of the first micrometer around the electrodes. This means that the pH changes which are created are no longer, or no longer to the full degree, effective in influencing or damaging the cells.

The pulse splitting (part ratio, amplitude ratio, form ratio) is selected on the basis of the application by taking into account the diffusion times and lengths of the protons and hydroxyl ions. Because the diffusion times and lengths in aqueous solutions can be estimated, the duration of the split pulse can be determined by means of the known diffusion formulae. For this purpose, the following formulation is to be used:

$$J_i = -D[dc_i/dx + ((z_i/Fc_i)/RT)d\Psi/dx]$$

where $J_i$ is the flux of the ion i, D is the diffusion coefficient, c is the concentration, x is the length, z is the charge number of the ion, $\Psi$ is the potential, T is the temperature, and F, R, Faraday and gas constants, respectively. For fluids which are of medical and biological interest, with lengths smaller than about 1 $\mu$m, times are derived in the range from a few $\mu$s up to a maximum of about 1 ms.

The duration of a partial pulse (partial pulse duration) is selected in such a way that it is shorter than or comparable to the diffusion time of the $H^+$ or $OH^-$ ion clouds created with the preceding partial pulse in each case. Accordingly, a spatial separation of the reaction products ($H^+$ and $OH^-$ ion clouds) is suppressed. Because the concentration of the $H^+$ or $OH^-$ ion clouds may be unsymmetrical, depending on the solution, an unsymmetrical part relationship of the partial pulse durations may be obtained. The switching time between the partial pulses is for preference substantially shorter than the partial pulse durations, and amounts to around 1 $\mu$s.

A decomposition of the desired pulse into more than two individual or partial pulses is particularly effective with longer or with a plurality of poration pulses (ms range) and leads, according to the invention, to the application of an AC voltage via an electronic gate circuit. Corresponding to the diffusion lengths referred to above, frequencies between about 1 kHz and about 1 MHz are preferred, and in particular about 10 kHz to about 800 kHz. Higher frequencies require an essential rise in the amplitude to exceed the breakdown voltage of the cell membranes. Lower frequencies can not be accommodated in the short period of the pulse duration.

The invention offers the following advantages. Processes and devices according to the invention can be effectively used for the pH-neutral or pH-compensated permeabilization and insertion and extraction, respectively, of molecules, liquids, organelles, and micro-particles for biotechnological, genetic engineering, and medical applications. They can equally be used for cell groups, cell-to-cell fusion, or aggregation of cells and microparticles or micro-organisms. The process makes it possible, in particular, for microelectrodes and extremely small spaces (about 10 to about 100 $\mu$m) to be used, such as can be created in Microsystems produced in semi-conductor technology. Although the objects to be dealt with during each pulse are subject to temporally-changing field directions, reliable and reproducible results can be achieved in the same way as with conventional electroporation. The poisoning of solutions due to dissolved electrode material is avoided and, accordingly, poration vessels (cuvettes in particular) can be used even with non-noble metals used as the electrodes.

Preferred applications of the invention are the provision of pH-neutral or pH-compensated electroporation devices and the construction of microsystems for handling or manipulation of biological cells between microelectrodes. A microsystem has characteristic dimensions of electrodes in the range from about 100 $\mu$m or less and characteristic dimensions of the intervals between the electrodes in the range of several cell diameters (e.g. about 2 to about 5).

The following explanation relates to pulse splitting according to the invention which can be implemented with conventional electroporation devices with the introduction of the appropriate measures. Accordingly, known details of electroporation devices, such as, in particular, the arrangement of the electrodes, the structure of the cuvette, etc. are not considered separately.

FIG. 1A shows the voltage path of a temporally cut capacitor discharge, which has been applied hitherto as a poration pulse at a pair of electrodes (prior art). The input amplitude U1 drops according to an exponential function. At a pulse time t1, which typically amounts from about 10 $\mu$ to about 100 ms, the poration pulse is switched off. For the duration of the pulse an acidation or alkalization takes place at the anode and cathode, respectively.

Figure 1B:
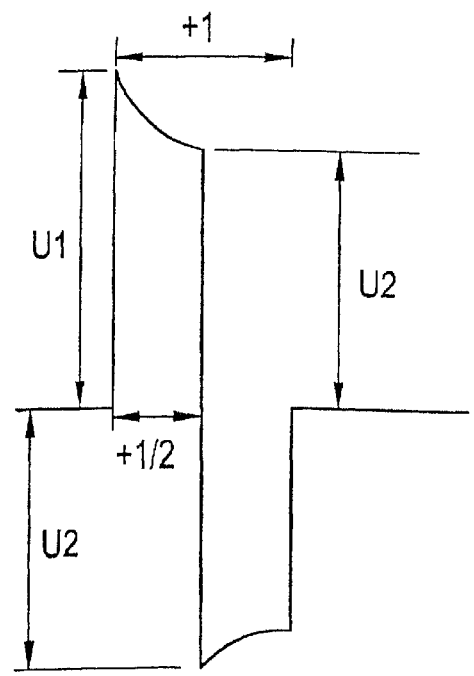

FIG. 1B shows the pulse decomposed according to the invention as a temporal voltage path between two electrodes, for example, with two partial pulses of different polarities. The capacitor discharge drops from the input amplitude U1 for the partial pulse duration t11 (in, this case t11=0.5·t1) of the first partial pulse, according to an exponential function. At the pulse time t11, which typically amounts to a few $\mu$s to a maximum of about 1 ms, the partial pulse is reversed. For the remaining period t12 (in this case t11=t12), the residual capacitor discharge is switched to the electrodes, up to the final amplitude U2, with reversed polarity. As a modification from the part ratio given here, t11=t12, other ratios of the partial pulse durations can be achieved.

It can be seen that, with the given amplitudes and times, the absolute value of the areas under the two pulses corresponds entirely to the area of the pulse in FIG. 1A. By reducing the amplitude as far as the polarisation change, a slight asymmetry pertains, which leads to a residual pH change. This can be compensated by a change in the part ratio, or, if with certain ion compositions of the media on the anodic and cathodic side the acidification or alkalization does not take place in the same amount, it can be used to compensate for these differences.

Figure 2A:
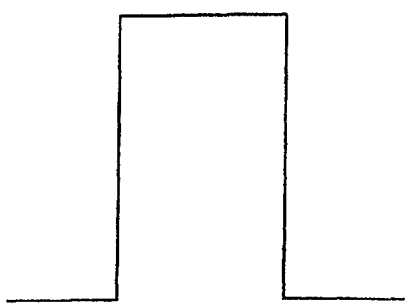
FIGS. 2A, 2B: a representation of splitting according to the invention of a square-wave poration pulse into partial pulses.
Figure 2B:
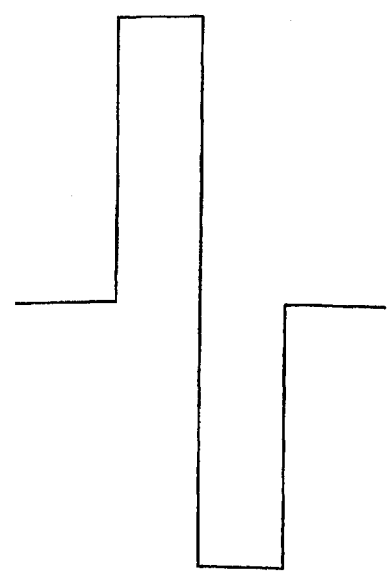

The asymmetry referred to in the use of discharge processes for pulse generation (asymmetric pulse forms) can also be prevented by the use of square-wave pulses. This is illustrated in FIGS. 2A and 2B. FIG. 2A shows the non-decomposed (conventional) poration pulse. According to the invention, during the course of the pulse the polarity is switched (FIG. 2B) so that two partial pulses are created. The power applied to each electrode is now substantially equal. In the corresponding manner, other pulse forms which can be created are also capable of decomposition.

Figure 3:
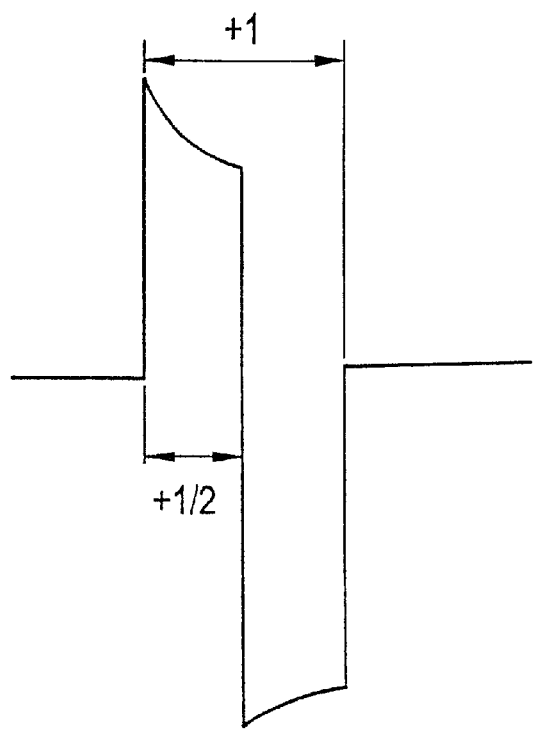
FIG. 3: a representation of splitting according to the invention of a square-wave poration pulse into partial pulses of different amplitudes.

The decomposition of a pulse into partial pulses of different amplitudes is illustrated in FIG. 3. According to this, for example, the amplitude of the first partial pulse is less than the amplitude of the second partial pulse. This is particularly preferred with the unsymmetrical electrolysis processes taking place at the electrodes, such as, for example, in suspension solutions containing chloride, in which chlorine may escape from the solution locally at an electrode. The amplitude splitting is effected in such a way that the lower $H^+$ or $OH^-$ formation (per time unit) is compensated in each case by a higher amplitude, and the total power of the intended poration pulse is retained. In addition, the partial pulse duration can be varied accordingly.

Figure 4:
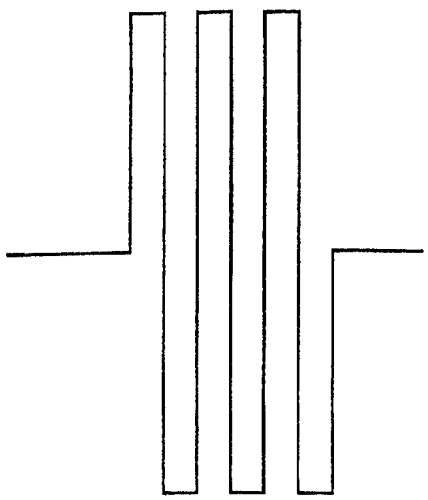
FIG. 4: a representation of splitting according to the invention of a square-wave poration pulse into a plurality of partial pulses.

FIG. 4 shows splitting a poration pulse into more than two pulses. For the almost complete compensation of the pH effect, an even-numbered decomposition is preferred. With very many decomposition pulses, however, an odd-numbered splitting can also be effected if the residual difference remains correspondingly small or the media require an asymmetry of the pulses.

Figure 5:
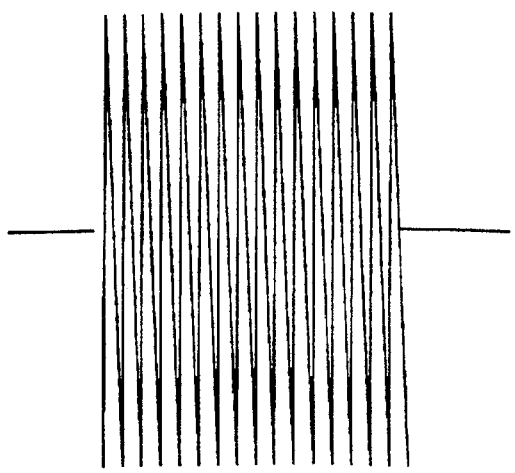
FIG. 5: a representation of application of an AC voltage for the duration of a poration pulse.

Alternatively, application of an AC voltage is also possible instead of a pulse switching at the electrodes. FIG. 5 shows application of a plurality of pulses in the form of an AC voltage via an electronic gate, this being released for the desired duration of the poration (corresponding to the pulse duration with the conventional process).

Figure 6:
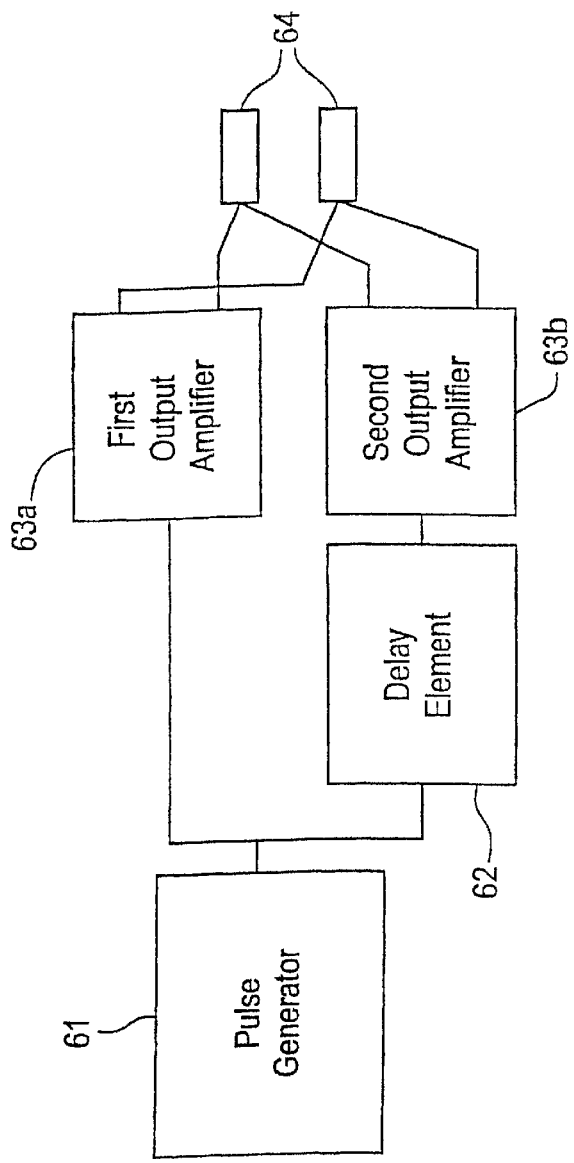
FIG. 6: a block circuit diagram of a control circuit of a poration device according to the invention.

A block circuit diagram of an electronic circuit with which the pulse decomposition can be effected is shown in FIG. 6. The reference number 61 designates a pulse generator, which creates the individual pulses in the conventional manner, but in this situation in each case with the shorter partpulse duration which is derived from the decomposition of the application-dependent pulse time desired into 2, 4, 6 or more partial pulses. The pulse generator 61 is connected, on the one hand, by means of a first output amplifier 63*a* to the electrodes 64 and, on the other, by means of a delay element 62 and a second output amplifier 63*b* to the electrodes 64. The second output amplifier 63*b* is a reversing amplifier. Each pulse accordingly first passes directly to the output amplifier 63*a* and the electrodes 64, and then, with a time delay, via the output amplifier 63*b*, with reversed polarity to the electrodes 64. The time delay is selected to be essentially equal to the pulse width.

The output amplifiers and the delay element allow for the adjustment of the individual amplification factors (amplitude asymmetry of the pulses) and the time delay, respectively, (asymmetry of the part ratio of the pulses). In addition, a pulse forming circuit can also be provided for. The partial pulses can have in particular rectangular, exponential, triangular, ramp-shaped or sine-shaped pulse forms.

In the event of a capacitor discharge being emulated, the pulse generator 61 is to be designed accordingly. One of a large number of known processes is the digitalization of the pulse. In this way, an asymmetry of the pulses can be created between the branch 61→63*a* and 61→62→63*b*, and, therefore, any desired pulse form can be implemented.

In the case of the use of very narrowly spaced electrodes (e.g. in Microsystems), pulse heights of a maximum of 100 V are needed to bring about a permeation of cells or their fusion. A large number of circuit variants of tri-state technology and push-pull stages of electronic technology are suitable for this.

Figure 7:
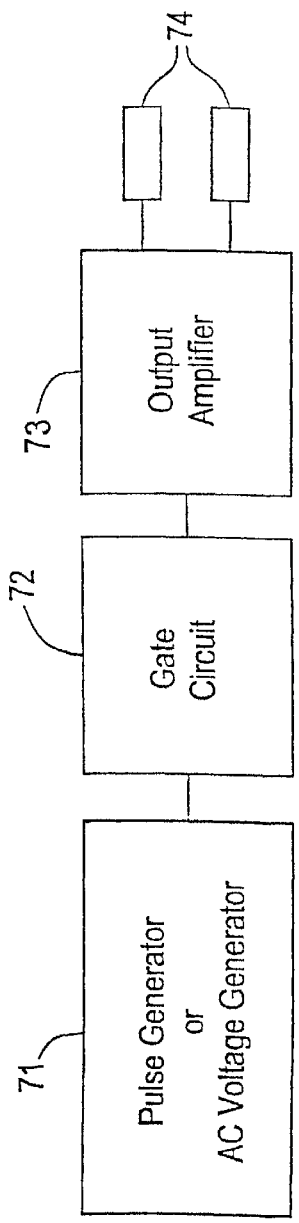
FIG. 7: a block circuit diagram of a control circuit with a gate circuit for the application of pulses or AC voltages.

FIG. 7 shows a block circuit diagram for application of the pulses or AC voltages under discussion via a gate. The reference number 71 designates a pulse generator or AC voltage generator, the signal of which passes via a gate circuit 72 for the period of the desired application to the output amplifier 73, and from there is available at the electrodes 74 for the permeation or fusion of the cells.

With arrangements of several pairs of electrodes, the pulse splitting according to the invention is carried out for each pair of electrodes. The circuits according to FIGS. 6 and to 7, respectively, are manifolded or adapted accordingly. If the electroporation is induced with several pulses, each of the pulses is broken down according to the invention.

The pulse splitting according to the invention can be applied to the treatment of any desired biological objects, including in particular biological objects such as, for example, biological cells or cell groups, or also synthetic objects such as liposomes, vesicles, or similar thereto.

What is claimed is:

1. A process for treating a biological or synthetic object subjected to an electrical field in a surrounding liquid medium for a predetermined pulse time (t1), said electrical field being formed by at least two electrodes comprising:

actuating at least once during the pulse time (t1) each of the electrodes as an anode and as a cathode, to cause at each electrode a polarity reversal and alternating electrolytic increases and reductions in pH of at least a portion of the liquid medium, subjecting the object during the pulse time (t1) to a number of electrical partial pulses which have a frequency in the range of 1 kHz to 1 MHz and which possess partial pulse durations, with sequentially reversing polarity or field direction such that the partial pulses possess sequentially varying partial pulse durations (t11, t12), pulse forms, and/or pulse amplitudes, and selecting the partial pulse durations (t11, t12), pulse forms, and/or pulse amplitudes such that, due to the electrolytic increases and reductions in pH value, substantially equal $H^+$ and $OH^-$ ion concentrations are created.

2. The process according to claim 1, in which the partial pulse durations are selected such that creation of $H^+$ or $OH^-$ ion concentrations at an electrode during a partial pulse is effected at least as rapidly as diffusion of $OH^-$ or $H^+$ ion concentrations created during a previous partial pulse from the electrode into the surrounding medium.

3. The process according to claim 1, wherein the partial pulses have, square-wave, exponential, delta-shaped, ramp-shaped, or sine-shaped pulse forms.

4. The process according to claim 1, wherein a permeation and/or fusion of cells or cell groups or of synthetic, membrane-encased structures, liposoma or vesicles, or the treatment of membrane-form or layer-form material is effected.

5. A device for treating a biological or synthetic object in a surrounding medium comprising at least two electrodes adapted to treat a biological or synthetic object in a surrounding medium, the medium connected to a pulse generator, wherein the pulse generator is connected to the electrodes via a control circuit arranged to impose on the electrodes, during a predetermined pulse time, at least two partial pulses of alternating reversed polarity or field direction, said pulses having a frequency in the range of 1 kHz to 1 MHz and the pulse generator providing the partial pulses in digitalized form for creation of asymmetries in pulse height, pulse path, or pulse length such that, due to the electrolytic increases and reductions in pH value, substantially equal $H^+$ and $OH^-$ ion concentrations are created.

6. The device according to claim 5, in which the control circuit comprises a first output amplifier, by means of which the pulse generator is connected to the electrodes for generation of said partial pulses with a first polarity, and a second output amplifier with a time delay element, by means of which the pulse generator is connected to the electrodes for generation of said partial pulses with a reversed polarity.

7. The device according to claim 5, wherein the pulse generator comprises at least one charge capacitor and the control circuit comprises a reversing switch, with which, during the pulse time, capacitor voltage is alternatingly switched to one of the electrodes.

8. The device according to claim 5, wherein the pulse generator generates an AC or tri-state voltage, and the control circuit comprises a gate circuit, which, during the pulse time, connects the pulse generator to the electrodes.

9. The device according to claim 5, wherein the pulse generator processes the partial pulses in digitalized form in adjustable amplitude and/or for emulation of any desired signal forms.

10. An electroporation device with an electropermeation or fusion chamber containing a device according to claim 5.

11. The electroporation device according to claim 10, which is a microsystem with a multi-electrode arrangement.

12. The electroporation device according to claim 11, wherein the microsystem possesses characteristic dimensions of the electrodes in the range from about 100 $\mu$m or less, and characteristic dimensions of the spaces between the electrodes are in the range of a few cell diameters.

* * * * *